United States Patent
Acien Alvarez et al.

(10) Patent No.: US 11,051,929 B2
(45) Date of Patent: Jul. 6, 2021

(54) NEOVAGINAL PROSTHESIS

(71) Applicants: UNIVERSIDAD MIGUEL HERNANDEZ, Alicante (ES); FUNDACION PARA EL FOMENTO DE LA INVESTIGACIÓN SANITARIA Y BIOMEDICA DE LA COMUNITAT VALENCIANA (FISABIO), Valencia (ES)

(72) Inventors: Pedro Acien Alvarez, Alicante (ES); Miguel Angel Oliva Meyer, Alicante (ES); Miguel Sanchez Lozano, Alicante (ES); Javier Martinez Garcia, Alicante (ES); Maria Isabel Acien Sanchez, Alicante (ES)

(73) Assignees: UNIVERSIDAD MIGUEL HERNANDEZ, Alicante (ES); FUNDACION PARA EL FOMENTO DE LA INVESTIGACION SANITARIA Y BIOMEDICA DE LA COMUNITAT VALENCIANA (FISABIO), Valencia (ES)

( * ) Notice: Subject to any disclaimer, the term of this patent is extended or adjusted under 35 U.S.C. 154(b) by 210 days.

(21) Appl. No.: 16/303,288

(22) PCT Filed: May 18, 2017

(86) PCT No.: PCT/ES2017/070332
§ 371 (c)(1),
(2) Date: May 1, 2019

(87) PCT Pub. No.: WO2017/203076
PCT Pub. Date: Nov. 30, 2017

(65) Prior Publication Data
US 2020/0060803 A1    Feb. 27, 2020

(30) Foreign Application Priority Data

May 23, 2016  (ES) .............................. ES201630650U

(51) Int. Cl.
*A61F 2/02*    (2006.01)
*A61F 2/04*    (2013.01)

(52) U.S. Cl.
CPC .................. *A61F 2/02* (2013.01); *A61F 2/04* (2013.01); *A61F 2230/0069* (2013.01); *A61F 2250/0059* (2013.01); *A61F 2250/0078* (2013.01)

(58) Field of Classification Search
CPC ........................................................ A61F 2/02
See application file for complete search history.

(56) References Cited

U.S. PATENT DOCUMENTS

| 6,224,580 B1* | 5/2001 | Christensen | .......... A61M 29/00 604/275 |
| 2012/0150105 A1* | 6/2012 | Canifax | .................... A61F 6/16 604/57 |

FOREIGN PATENT DOCUMENTS

| CN | 101991476 A | 3/2011 |
| CN | 203263597 U | 11/2013 |

OTHER PUBLICATIONS

Coskun, et al, "The use of a silicone-coated acrylic vaginal stent in McIndoe vaginoplasty and review of the literature concerning silicone-based vaginal stents: a case report", BMC Surgery, 2007, 7:13. (Year: 2007).*

(Continued)

*Primary Examiner* — Leslie Lopez
(74) *Attorney, Agent, or Firm* — Hayes Soloway PC

(57) ABSTRACT

The invention relates to a neovaginal prosthesis formed by an essentially cylindrical hollow main body comprising a (Continued)

closed upper end and an open lower end, and a securing plate intended to connect to the lower end of the main body.

6 Claims, 2 Drawing Sheets

(56) References Cited

OTHER PUBLICATIONS

Coskun et al.; "The use of a silicone-coated acrylic vaginal stent in McIndoe vaginoplasty and review of the literature concerning silicone-based vaginal stents: a case report"; BMC Surgery; Jul. 10, 2007; p. 1-4; 7:13; BioMed Central Ltd.
Keser et al.; "Treatment of vaginal agenesis with modified Abbe-McIndoe technique: long-term follow-up in 22 patients"; European Journal of Obstetrics & Gynecology; 2005; p. 110-116; 121; Elsevier.

* cited by examiner

NEOVAGINAL PROSTHESIS

CROSS-REFERENCE TO RELATED APPLICATIONS AND PRIORITY

This patent application claims priority from PCT Patent Application No. PCT/ES2017/070332 filed May 18, 2017, which claims priority from Spanish Patent Application No. ES U201630650 filed May 23, 2016. Each of these patent applications are herein incorporated by reference in their entirety.

OBJECT OF THE INVENTION

The present invention is included in the technical field of prostheses that can be implanted in the body, more specifically those prosthesis with hollow or tubular geometry, and it relates in particular to a prosthesis designed to be inserted in the body after vaginoplasty interventions for the creation of a vagina or neovagina.

BACKGROUND OF THE INVENTION

Rokitansky syndrome or Mayer-Rokitansky-Küster-Hauser syndrome (MRKHS) is a clinical congenital malformation picture due to severe disorders in the development of the Müllerian ducts, whereby phenotypically female patients have an absence of vagina and uterus but they have functional ovaries. The main symptom is primary amenorrhea, i.e. failure in the appearance of the menarche or first period of the menstrual cycle.

A woman with this syndrome has normal production of female hormones, so that she reaches puberty she will develop her female sexual characteristics, including ovulation. However, there is no menstruation as the uterus and vagina are lacking. Some patients may have a uterus, i.e. the uterine body with normal endometrium, or have only a cavitated uterine horn with endometrium, but where the uterus neck and vagina are missing, and therefore, they have menstruation that is concealed or retrograde to the abdomen, due to vaginal or cervical-vaginal agenesis. The absence of vagina is generally total, also making sexual relations with vaginal penetration impossible.

Other patients who also have total absence of vagina are those cases with complete androgen insensitivity syndrome (CAIS), and Morris syndrome; as occurs with transsexual people.

There are various surgical techniques designed to correct agenesis or lack of vagina. Among said techniques, the most typical is that called McIndoe technique, wherein a space is defined between the bladder and the rectum by surgical dissection wherein a prosthesis is inserted for the definition and maintenance by dilatation of the surgically neoformed neovaginal cavity, where said prosthesis is generally covered with a free skin graft of partial or total thickness, typically taken from the thick, the buttock or the hypogastric region to cover the neoformed space with skin, so that it results like a normal epidermized or epithelialized vagina.

This prosthesis is removed after an estimated time that generally varies between seven and ten days, the time in which the skin graft will have covered the neoformed vaginal space, later using the actual prosthesis or a dilator for the definition and maintenance of a suitable vaginal luminar diameter during a further approximately 6 weeks, the time after which, should additional complications not arise, the patient can start normal sexual activity. It is recommended from that time to maintain said prosthesis, at least during night-time periods, to avoid the decrease due to retraction of said luminar diameter.

In the current state of the art, various devices are known that are designed to dilate the surgically defined space for creation of a neovagina, among which we can highlight dilators equipped with an expanding ball, vaginal stents and prostheses. Said current prosthesis have different problems, among which we can highlight in first place their unanatomical design and the need for external coatings obtained from the patient's own skin. Furthermore, they are usually very heavy and uncomfortable for the user, they can even cause ulcers due to decubitus in the intestine or on the urethra.

DESCRIPTION OF THE INVENTION

The object of the invention consists of a prosthesis designed to be temporarily inserted in the space defined between the bladder and the rectum of women with vaginal agenesis and in sex-change operations by means of the surgical intervention known as McIndoe technique, to create an artificial vaginal cavity or neovagina with a suitable luminal diameter. Therefore, the neovaginal prosthesis comprises an essentially cylindrical hollow main body, with external diametric dimensions in reduction from a first upper end to a second lower end. The upper end is designed to be inserted inside the surgically defined space, whilst the lower end remains outside, protruding slightly from the vaginal opening. An optional securing plate additionally guarantees the connection between the main body and the patient's anatomy.

The upper end of the main body has an essentially rounded geometry, with a first through-orifice defined in its surface for drainage of liquids and secretions towards the outside through the hollow interior of said main body. The lower end comprises a second through-orifice to allow the exit of the liquids collected.

A side notch is defined in the proximity of said lower end of the main body to protect the anatomical area of the patient's urethra, in the proximity of which the prosthesis is inserted. This prosthesis is also dimensioned to minimally protrude from the vaginal opening, beneficially resulting in comfort and safety, so that it can also be maintained in its correct position by the vulva and pelvic floor muscles.

In a preferred embodiment, the prosthesis is executed by means of 3D printer modelling, using polylactic acid, also called PLA, as main material, which gives a prosthesis a reduced weight. PLA is also a biocompatible material and stimulating of epithelial regeneration.

The design is devised so that the surgical technique of creation of a neovagina known as McIndoe technique may be done without the need for skin grafts, i.e. using only the prosthesis with an additional coating thereof with biocompatible and biodegradable mesh instead of skin grafts from the patient, thus making the surgery less invasive and simpler, reducing subsequent dermal scars and giving the user greater comfort and functionality. This prosthesis shall also be applicable as a vaginal mould in the case of wanting to perform the traditional McIndoe technique with a skin graft from the patient's skin.

DESCRIPTION OF THE DRAWINGS

To complement the description being made and in order to aid towards a better understanding of the characteristics of the invention, in accordance with a preferred example of practical embodiment thereof, a set of drawings is attached as an integral part of said description wherein, with illustrative and non-limiting character, the following has been represented.

PREFERRED EMBODIMENT OF THE INVENTION

A detailed explanation of the example of preferred embodiment of the object of the present invention is provided below, with the aid of the aforementioned figures.

Figure 1:
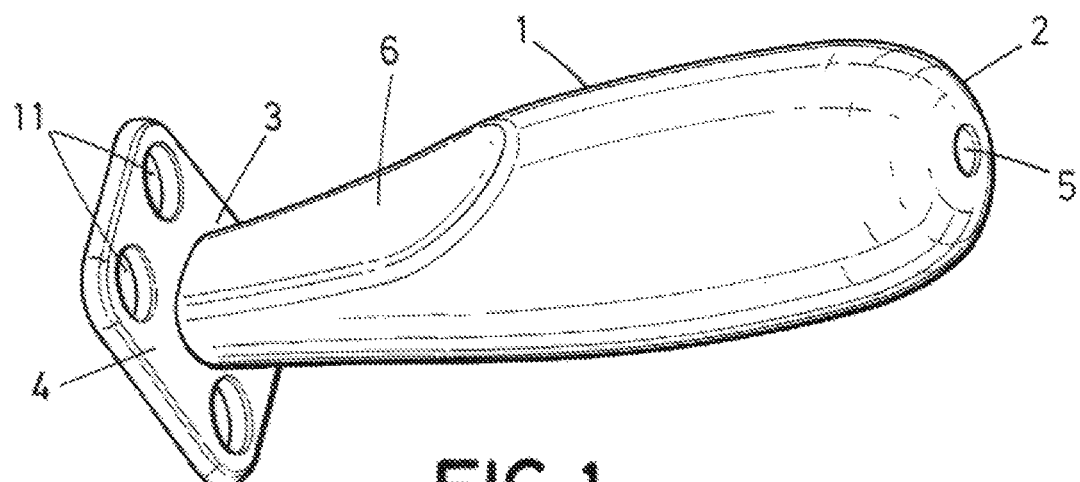
FIG. 1—Shows a top perspective view of the prosthesis, wherein its main constituent elements are observed.

The neovaginal prosthesis disclosed is formed by an essentially cylindrical hollow main body (1) which comprises a closed upper end (2) and an open lower end (3), and a securing plate (4) designed to be connected to the lower end (3) of the main body (1), as shown in FIG. 1.

The main body (1) is designed to be temporarily inserted in a space defined between the bladder and the rectum of a patient with vaginal agenesis by means of the McIndoe surgical technique, to create a vaginal cavity or neovagina with a suitable luminar diameter by means of dilatation. To do this, the upper end (2) has an essentially rounded geometry in the centre whereof a first orifice (5) is defined, to allow the drainage of liquids and secretions through the hollow interior of the main body (1).

Figure 3:
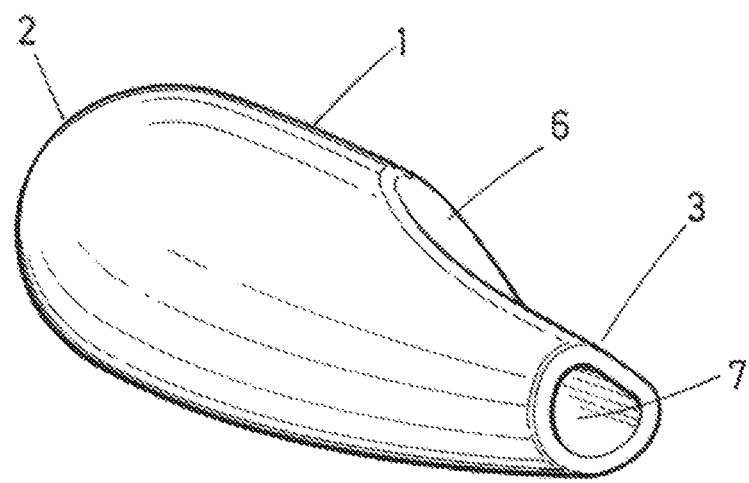
FIG. 3—Shows a bottom perspective view of the prosthesis.

The main body (1) additionally comprises a side notch (6) defined in the proximity of its lower end (3) to facilitate the coupling of the prosthesis in the proximity of the urethra without pressing on it. A second orifice (7) is defined in the centre of the lower end (3), shown in FIG. 3, firstly designed to allow the drainage of liquids from the hollow interior of the main body (1) and in second place to provide the connection of the securing plate (4) with said main body (1). It additionally anticipates the definition of a third orifice (8) designed to house an extraction thread (9) to facilitate the extraction of the prosthesis.

Figure 2:
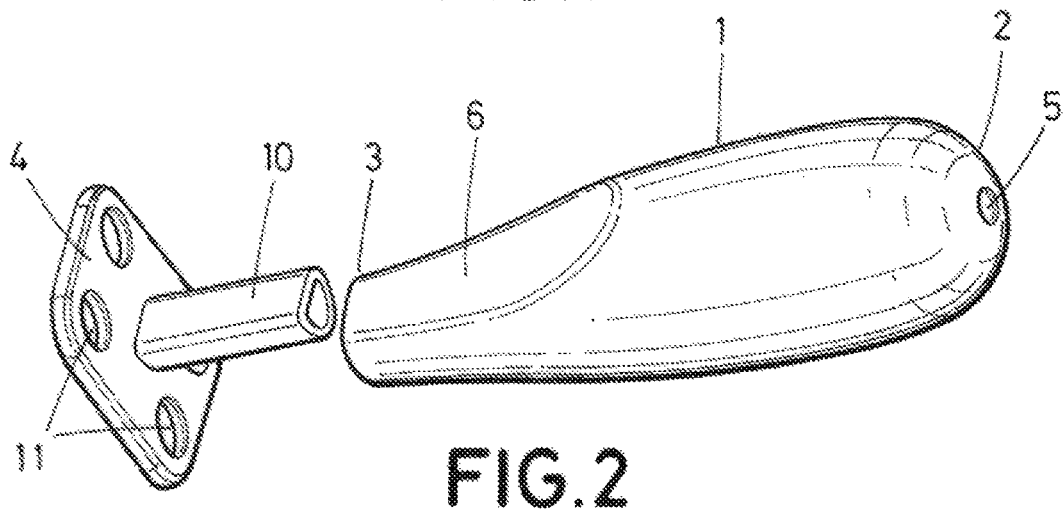
FIG. 2—Shows a view similar to that of FIG. 1, wherein the coupling between the main body and the securing plate are illustrated.

The securing plate (4), shown in FIG. 2, is designed to be perpendicularly connected to the lower end (3) of the main body (1) to allow its anatomical securing to the patient's body through tapes, not represented in the attached figures, designed to be knotted round the waist.

To do this, said securing plate (4) comprises a hollow protuberance (10) which is projected from its geometric centre, with a geometry and dimensions such that they facilitate its concentric insertion inside the second orifice (7) of the main body (1) in turn allowing the evacuation of liquids towards the outside. Additionally, a plurality of through-openings (11) defined in the securing plate (4) are designed to be traversed by the aforementioned securing tapes.

Figure 4:
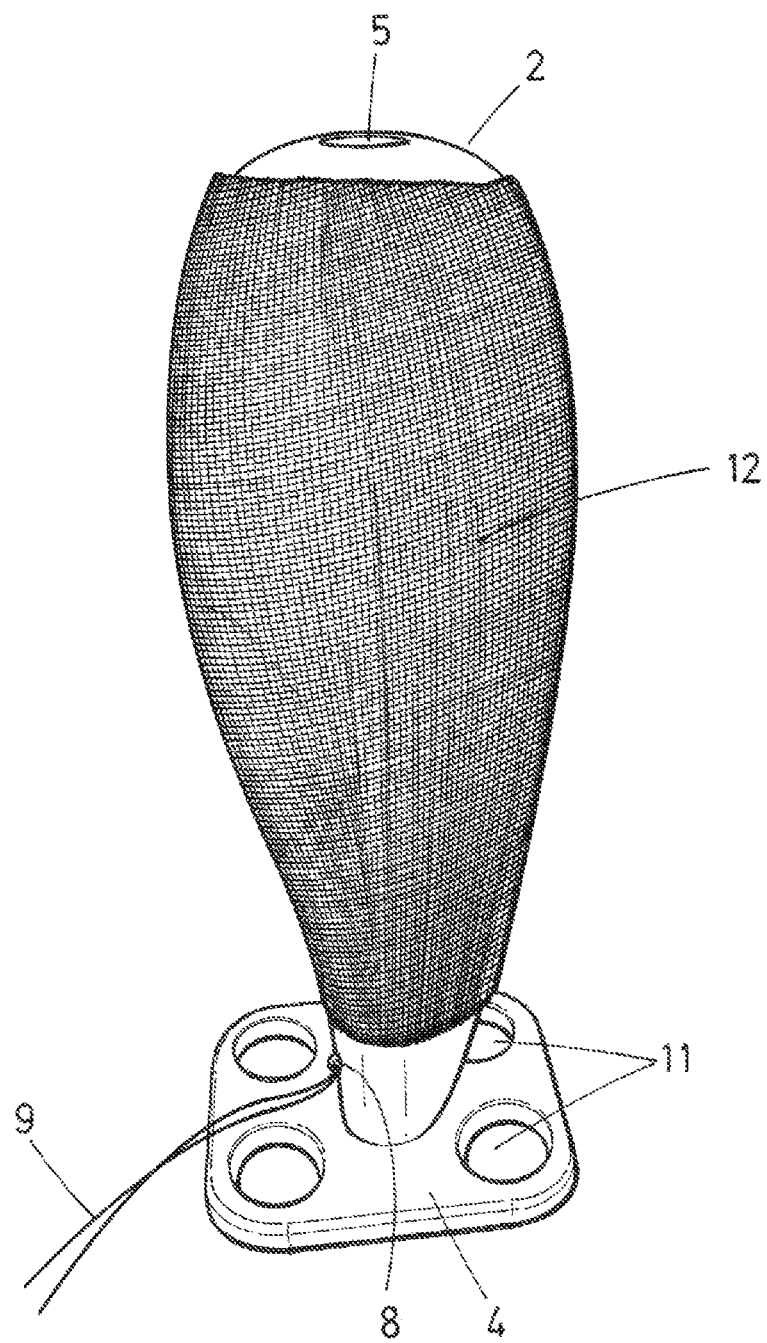
FIG. 4—Shows a front perspective view of the prosthesis coated by a mesh.

It additionally contemplates the incorporation of a mesh (12) designed to cover the main body (1) of the prosthesis as shown in FIG. 4 and replace in that way the skin graft that is normally performed in the aforementioned technique. To do this, said mesh (12) is made in a biocompatible and biodegradable material which acts as base for the biological generation of tissues, also known as epithelialization, around it and to avoid the adherence of the prosthesis to the surrounding tissues during its surgical insertion. In this case, the securing plate (4) has the additional function of maintaining in vertical position, as shown in FIG. 4, on a surgical table to proceed with its coating with a mesh (12) before its insertion.

The invention claimed is:

1. A neovaginal prosthesis, designed to be temporarily inserted through a vaginal opening in a vaginal cavity with a determined luminar diameter, comprising
   a hollow main body, defining an outside of the hollow main body and an inside of the hollow main body, which in turn comprises:
   a closed end of rounded geometry, designed to be inserted inside the vaginal cavity,
   a first orifice defined in the closed end to allow drainage of liquids and secretions towards the inside of the hollow main body,
   a first intermediate cylindrical section located proximate the closed end,
   a second intermediate section located proximate the first intermediate cylindrical section, opposite to the closed end, that has a progressively decreasing diameter,
   an open end proximate the second intermediate section, opposite to the first intermediate cylindrical section, designed to remain outside of the vaginal cavity, protruding slightly from the vaginal opening,
   a side notch defined in the second intermediate section to facilitate a coupling the neovaginal prosthesis in a proximity of an urethra without pressing on the urethra,
   a second orifice defined in the open end, designed to allow drainage of the liquids and secretions from the inside of the hollow main body towards the outside of the hollow main body,
   a securing element designed to be connected to the open end of the main body which is fitted with,
   a securing plate provided with a plurality of through-openings designed to be traversed by additional tapes, and
   a hollow protuberance extending from the securing plate, designed to be concentrically inserted inside the second orifice of the hollow main body to evacuate the liquids and secretions towards the outside of the hollow main body.

2. The neovaginal prosthesis of claim 1 wherein the neovaginal prosthesis additionally comprises a mesh made in a biocompatible and biodegradable material, designed to cover the hollow main body, acting as a base for a generation of tissues, to facilitate epithelialization of the vaginal cavity around the hollow main body.

3. The neovaginal prosthesis of claim 1, wherein the neovaginal prosthesis additionally comprises a third orifice defined in the open end, designed to house an extraction thread to facilitate extraction of the neovaginal prosthesis.

4. The neovaginal prosthesis of claim 1, wherein the hollow main body comprises polylactic acid (PLA).

5. The neovaginal prosthesis of claim 1, wherein the hollow main body additionally comprises a surface coating of anti-adherent material to facilitate an insertion and extraction of the neovaginal prosthesis by a patient.

6. The neovaginal prosthesis of claim 5, wherein the coating of anti-adherent material comprises silicone.

* * * * *